(12) United States Patent
Cable, II et al.

(10) Patent No.: US 11,654,014 B2
(45) Date of Patent: May 23, 2023

(54) IOL WITH DRUG DELIVERY DEVICES AND UNINTERRUPTED PCO BARRIER EDGE

(71) Applicants: SpyGlass Pharma, Inc., Aliso Viejo, CA (US); The Regents of the University of Colorado, a body corporate, Denver, CO (US)

(72) Inventors: Craig Alan Cable, II, Laguna Hills, CA (US); Glenn R. Sussman, Laguna Niguel, CA (US); James R. Dennewill, Laguna Niguel, CA (US); Malik Y. Kahook, Denver, CO (US)

(73) Assignees: SpyGlass Pharma, Inc., Aliso Viejo, CA (US); The Regents of the University of Colorado, Denver, CO (US)

( * ) Notice: Subject to any disclaimer, the term of this patent is extended or adjusted under 35 U.S.C. 154(b) by 0 days.

(21) Appl. No.: 17/540,212

(22) Filed: Dec. 1, 2021

(65) Prior Publication Data
US 2022/0104937 A1  Apr. 7, 2022

Related U.S. Application Data

(63) Continuation of application No. 17/062,909, filed on Oct. 5, 2020.

(51) Int. Cl.
*A61F 2/16* (2006.01)
(52) U.S. Cl.
CPC .......... *A61F 2/16* (2013.01); *A61F 2002/169* (2015.04); *A61F 2250/0067* (2013.01)

(58) Field of Classification Search
None
See application file for complete search history.

(56) References Cited

U.S. PATENT DOCUMENTS

| | | | |
|---|---|---|---|
| 2009/0130176 A1 | 5/2009 | Bossy-Nobs et al. | |
| 2010/0204788 A1 | 8/2010 | Van Noy | |
| 2014/0148900 A1 | 5/2014 | Ratner et al. | |
| 2018/0368974 A1* | 12/2018 | Kahook | A61F 2/1648 |
| 2020/0022840 A1 | 1/2020 | Kahook et al. | |
| 2020/0405538 A1 | 12/2020 | Mandell | |

FOREIGN PATENT DOCUMENTS

| | | |
|---|---|---|
| EP | 1543799 | 6/2005 |
| EP | 3210572 | 8/2017 |
| GB | 2586420 B | 11/2021 |
| WO | WO2008113043 | 9/2008 |

(Continued)

OTHER PUBLICATIONS

Combined Search and Examination Report from UK Patent Application No. 2017747.3 dated Dec. 16, 2020.

(Continued)

*Primary Examiner* — Leslie Lopez
(74) *Attorney, Agent, or Firm* — Polsinelli PC (57) ABSTRACT

An ophthalmic implant including an IOL with haptics, and drug delivery devices secured to the haptics. The posterior-most extent of the drug delivery device is located anterior to the posterior edge or PCE barrier edge, of the IOL. In other configurations, the drug delivery devices are provided with PCO barrier edges.

26 Claims, 5 Drawing Sheets

(56) References Cited

FOREIGN PATENT DOCUMENTS

WO      2014027963  A1      2/2014

OTHER PUBLICATIONS

International Search Report and Written Opinion for Application No. PCT/US2021/053629, dated Feb. 2, 2022, 19 Pages.
Combined Search and Examination Report from GB Patent Application No. 2113232.9 dated Dec. 8, 2021, 4 pages.
U.S. Patent and Trademark Office Action, Non-Final Office Action, U.S. Appl. No. 17/947,001, filed Dec. 15, 2022, 14 pages.
U.S. Patent Office Action, Non-Final Office Action, U.S. Appl. No. 17/947,001, filed Dec. 15, 2022, 14 pages.

* cited by examiner

IOL WITH DRUG DELIVERY DEVICES AND UNINTERRUPTED PCO BARRIER EDGE

CROSS-REFERENCE

This application is a continuation of U.S. patent application Ser. No. 17/062,909, filed Oct. 5, 2020, which is incorporated herein by reference in its entirety and to which application we claim priority under 35 USC § 120.

FIELD OF THE INVENTIONS

The inventions described below relate to the field of ophthalmic implants such as intraocular lenses.

BACKGROUND OF THE INVENTIONS

Intraocular lenses (IOL's) are artificial lenses for the eye that can be implanted to replace the natural lens of a patient's eye after the natural lens is removed. The natural lens might be removed because it is affected by cataracts, and the IOL can be implanted to provide clear vision and some degree of focusing to the patient. An intraocular lens may also be implanted in a patient without removing the natural lens (a phakic intraocular lens or PIOL), to correct extreme near-sightedness or far-sightedness. It is advantageous to administer some therapeutic agents to the eye, coincident with implantation of the IOL, to alleviate various side effects of the IOL or treat other conditions of the eye that might coexist with the conditions that lead to cataracts. Side-effects such as infection and inflammation, and conditions such as glaucoma, can be treated with therapeutic agents that may be incorporated into additional devices that may be secured to the IOL. In addition to IOL's, ocular implants not including lenses may be implanted to address various other conditions.

Posterior capsular opacification (PCO) is a condition that affects some IOL implantations, and occurs due to migration of lens epithelial cells into the region between the IOL and the posterior portion of the lens capsule. As these lens epithelial cells proliferate and differentiate in this region, the posterior portion of the lens capsule becomes opaque. This can cause visual impairment, sometimes referred to as a secondary cataract. This effect may be limited by the structure of the IOL itself, such as forming the IOL with a posterior surface and circumferential side wall surface joined with a sharply angular edge (typically referred to as a square edge). The posterior portion of the lens capsule collapses onto the IOL, and fuses to the IOL, and the fused join between the posterior portion of the lens capsule and the sharply angular edge of the IOL serves as a barrier to lens epithelial cells.

Previous patent applications, such as Kahook, et al., Ophthalmic Device For Drug Delivery, U.S. Pub. 2020/0022840 (Jan. 23, 2020) disclose various configurations of drug delivery devices to be used in conjunction with IOL's. Others have proposed placement of drug delivery devices on haptics. For those situations in which placement of the drug delivery devices on the haptics is preferred, we propose configurations that do not disrupt the square edge needed to block migration of lens endothelial cells to the back side of the IOL.

SUMMARY

The devices and methods described below provide for placement of drug delivery devices on IOL haptics while preserving a PCO barrier edge around the entire periphery of the back side of the IOL. The configuration may be employed with IOL's and other ophthalmic implants. The configuration allows implantation of an IOL along with implantation of drug delivery devices to treat various conditions affecting implant patients while maintaining a PCO barrier which is effective around the entire periphery of the IOL. The device includes an IOL assembly comprising a lens, and a haptic. The IOL assembly is characterized by an anterior surface and a posterior surface, and a circumferential side wall, wherein the posterior surface joins the circumferential side wall in a sharply angular edge, where the sharply angular edge defines a plane of the sharply angular edge, and the sharply angular edge is functional as a PCO barrier edge. The drug delivery devices are disposed on the haptics, and are configured and disposed on the haptic such that a posterior-most surface of each drug delivery device is anteriorly displaced from the plane. With this construction, the presence of the drug delivery devices on the haptics do not disrupt formation of a PCO barrier between the sharp edge and the posterior portion of the lens capsule.

In another configuration which preserves a PCO barrier edge, the posterior-most extent of the drug delivery device may extend posteriorly beyond the plane of the PCO barrier edge of the lens. In this configuration, the drug delivery device is configured with a posterior surface and a circumferential side wall adjacent the posterior side wall, and, like the PCO barrier edge of the IOL described above, the posterior surface of the drug delivery device joins the circumferential side wall of the drug delivery device in a sharply angular edge (also a posterior-lateral edge).

Additionally, other configurations of the drug delivery device described below provide for stable positioning of the IOL and drug delivery device within the capsular bag. The anterior surface of the drug delivery device is configured such that forces exerted on the drug delivery device by the capsular bag do not promote tilting of the IOL relative to the equatorial plane of the capsular bag, so that the optical axis of the IOL lens is not angled relative to the optical axis of the eye. The posterior surface may be a flat surface parallel to the plane of the IOL, or a curved surface bounded by an edge which lies in a plane parallel to the plane of the IOL.

DETAILED DESCRIPTION OF THE INVENTIONS

Figure 1:
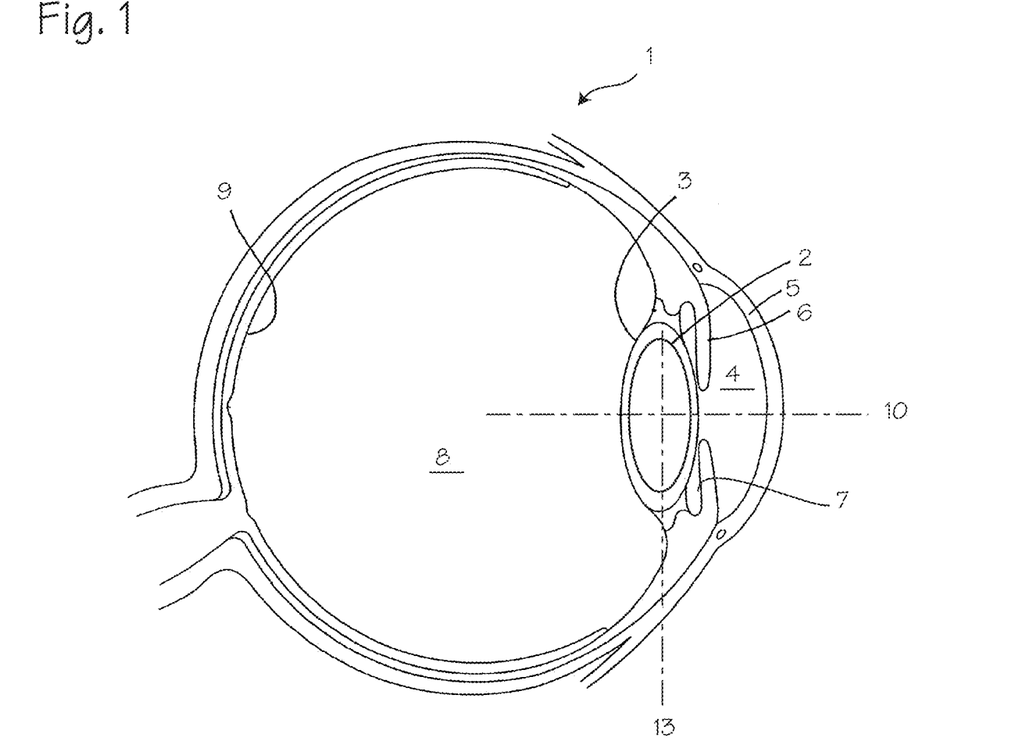
FIGS. 1 and 2 illustrate the environment of use of an ophthalmic implant system for drug delivery.
Figure 2:
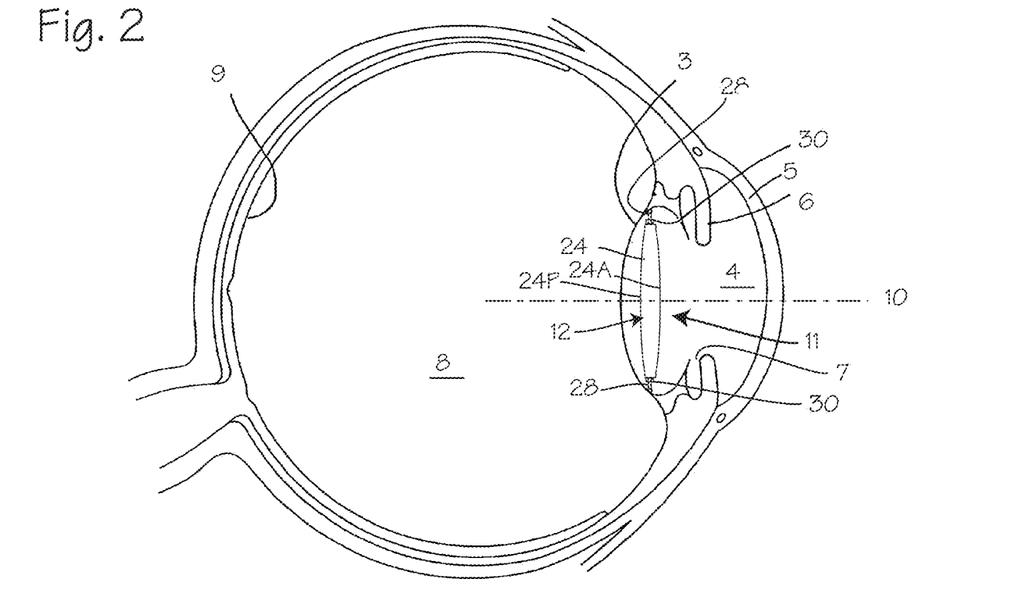

FIGS. 1 and 2 illustrate placement and use of an IOL (or other ophthalmic implant system) in the eye of a patient. The eye 1 includes a lens 2 (the natural lens of the eye) and lens capsular bag 3, and the anterior chamber 4 which includes the cornea 5 and iris 6 and aqueous humour filling the space between the cornea and the iris, and a posterior chamber 7 between the iris and the capsular bag. The posterior cavity/vitreous body 8 is the large space between the lens and the retina 9. The natural lens 2 of the eye is characterized by an optical axis 10. The capsular bag is characterized by an equatorial plane 13, which is generally perpendicular to the optical axis. (In the following description of the ophthalmic implant and/or intraocular lens system, the terms posterior and anterior will be used in relation to the anatomy of the eye, in which the cornea is anterior and the retina is posterior.)

FIG. 2 illustrates a placement of the IOL system (or other ophthalmic implant system) 11 in the eye including the intraocular lens assembly 12 and drug delivery device 30 which is implanted in the capsular bag in conjunction with the intraocular lens assembly 12. As shown in FIG. 2, and in more detail in FIGS. 3 through 5, the drug delivery device 30 is disposed on the haptics 28. The intraocular lens assembly 12 includes a lens 24 and one or more haptics 28, and one or more drug delivery devices 30. The intraocular lens assembly 12 is characterized by an anterior surface 24A and a posterior surface 24P and a circumferential side wall surface 24C. Other ophthalmic implants such as a capsular tension ring, or a capsular scaffold for holding the drug delivery devices in place may take the place of the IOL. The haptics may be any form of haptic, such as C-loops or J-loops.

Figure 3:
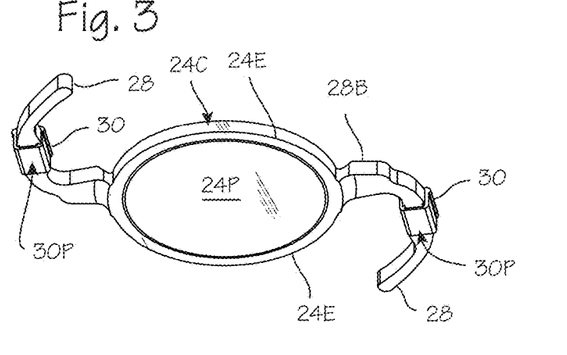
FIG. 3 is a view of the IOL and drug delivery devices, showing the posterior aspect of the device.

FIG. 3 is a view of the IOL 12 and drug delivery devices 30, showing the posterior aspect of the device, including the posterior surface 24P of the lens 24, and the sharply angular posterior-lateral edge 24E of the IOL, which may be the edge of the lens proper, or the edge of a frame surrounding the lens. The joint 31 between the haptic and the lens is preferably displaced/offset anteriorly from the sharp edge, to retain the PCO edge entirely around the periphery of the posterior side of the lens. (Typically, the lens and haptics will be integrally formed, and this "joint" refers to the transition between the lens and the haptic.) A drug delivery device 30 is disposed on one or both haptics 28 (preferably both), secured in any suitable manner, such as a friction fit of the tubular (rectangular or cylindrical) drug delivery device slipped over the haptic. The drug delivery device is characterized by a posterior surface 30P, facing posteriorly just as the posterior surface 24P of the lens does. The posterior surface 30P is also displaced/offset anteriorly from the posterior-lateral edge 24E, to avoid disruption of the fusion of the posterior capsule 3 to the posterior-lateral edge 24E. For completeness, FIG. 4 is a view of the IOL and drug delivery devices, showing the anterior aspect of the device, including the anterior surface 24A of the lens 24, each haptic 28, and the drug delivery devices 30 secured to the haptics.

The front edge of the IOL, at which point the anterior surface 24A meets the circumferential side wall surface of the IOL, may be a sharply angular edge comparable to the edge 24E on the posterior side of the IOL, or may be rounded or configured to obtain desired optical characteristics.

Figures 4, 5:
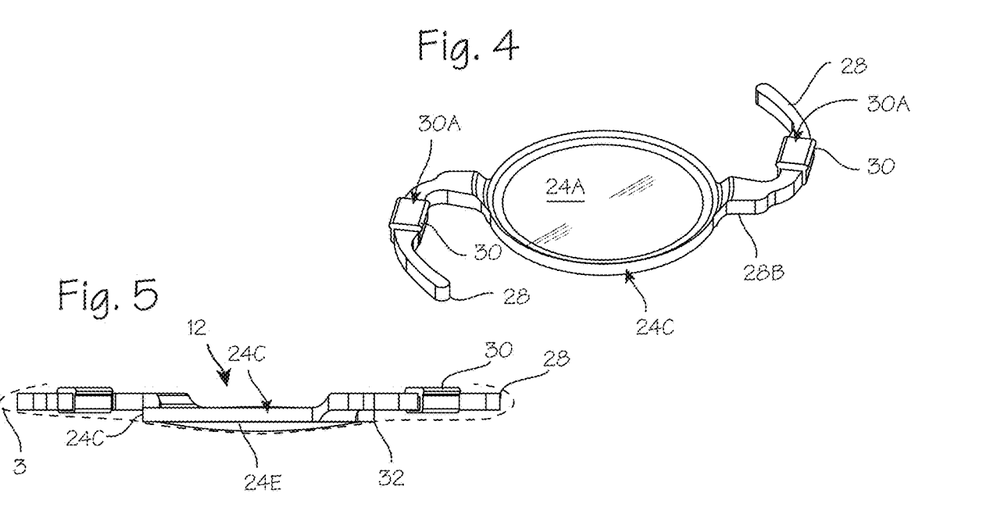
FIG. 4 is a view of the IOL and drug delivery devices, showing the anterior aspect of the device.
FIG. 5 illustrates the intraocular lens and drug delivery devices, illustrating the anterior offset of the haptics and drug delivery devices.
Figure 6:
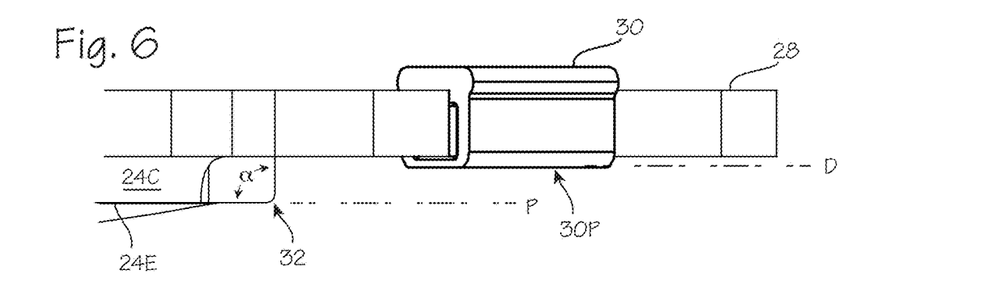
FIG. 6 illustrates the sharply angular edge of the IOL.

FIG. 5 illustrates the intraocular lens assembly 12, including the lens 24, one or more haptics 28, and one or more drug delivery devices 30. As shown in FIG. 5, the sharp edge 24E between the posterior surface 24P of the IOL and circumferential side wall surface 24C is an edge that circumscribes the lens 24 (preferably entirely circumscribes the lens), and establishes a plane (P) in which the sharp edge lies. The posterior-most extent of the drug delivery devices and optionally, the joint between the haptic and the lens is displaced anteriorly from this plane, not extending posteriorly to the plane (P) established by the sharp posterior edge of the IOL. In FIG. 6, the plane of the sharp posterior edge is marked as plane (P). The posterior extent of the drug delivery devices attached to the haptics is limited (and, optionally, the haptic joint), for example, by an offset represented by plane D. The offset is sufficient to avoid disruption of the fusion of the posterior portion of the capsule with the sharp angular edge 24E, and may be 0.1 to 1.0 mm. The sharply angular edge 24E may be any edge configured to function as a PCO barrier edge, and may be characterized by, for example, and inside angle ☐ of 80-100°, and a corner radius 32 of less than 500 um, and preferably less than 60 um. This is illustrated in FIG. 6.

As shown in FIG. 5, the natural lens capsule 3 (shown in phantom) has collapsed onto the IOL, and, along the line at which the capsule meets the sharp edge 24E, and this forms an effective barrier against migration of the lens endothelial cells from the anterior chamber into the space posterior to the IOL, between the IOL posterior surface and the capsule posterior surface.

The drug delivery devices may be provided in many configurations. As illustrated in the figures, the drug delivery devices may be configured as a collar or sleeve with a through-hole, which can be slipped over the haptic and retained with a friction fit or detent arrangement. The drug delivery devices may comprise a polymer matrix with therapeutic agents embedded in the matrix, or it may be comprised of a therapeutic agent in an erodible form. The matrix preferably comprises silicone, though other suitable matrix material may be used. The entirety of the drug delivery device may comprise the matrix material loaded with therapeutic agent, or an erodible therapeutic agent, or the matrix material loaded with therapeutic agent, or an erodible therapeutic agent may be limited to portions of the drug delivery device, while the remaining portions are provided for structure.

In use, the IOL assembly of FIGS. 3 through 6 with the drug delivery device configured and disposed on the haptic such that a posterior-most surface of the drug delivery device will be anteriorly displaced from the plane (P) once installed so that the presence of the drug delivery device on the haptic does not disrupt formation of a PCO barrier with the PCO barrier edge of the IOL lens when implanted within a capsular bag of an eye of the patient; and thereafter the capsular bag will approximate the IOL, and form a PCO barrier between the posterior portion of the capsular bag and the sharply angular edge uninterrupted by the posterior of the drug delivery device.

Figure 7:
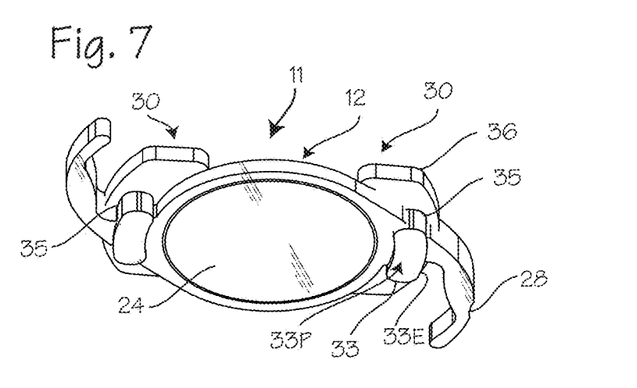
FIGS. 7 and 8 illustrate an IOL and drug delivery device combination in which the drug delivery device posterior is provided with a PCO barrier edge distinct from the PCO barrier edge of the IOL.
Figure 8:
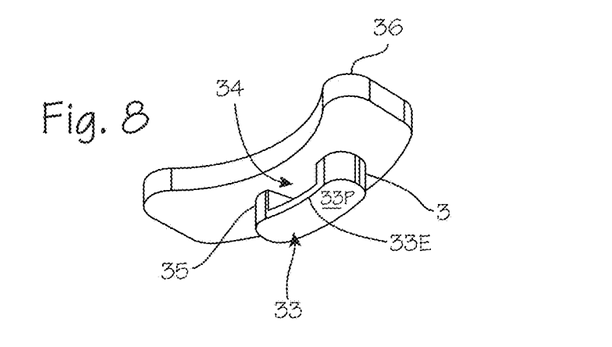
Figure 10:
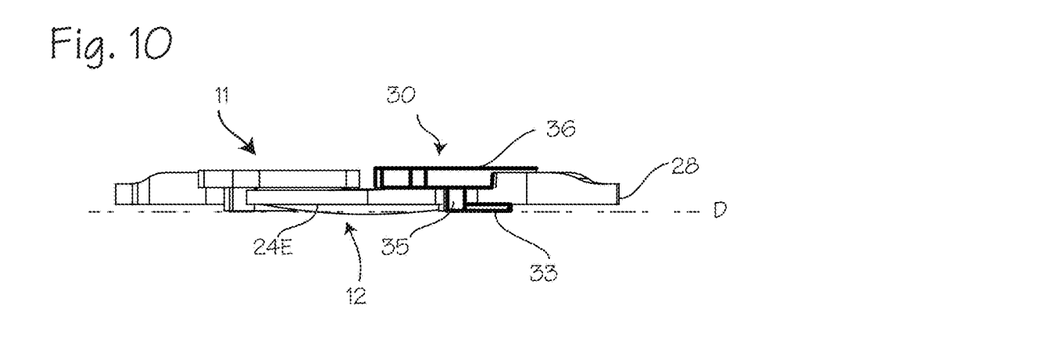
FIG. 10 illustrates a configuration in which the plane (D) is posteriorly displaced from the plane (P) defined by the PCO barrier edge 24E of the IOL.

FIGS. 7 and 8 illustrate an IOL 12 and drug delivery device 30 assembled, in which the drug delivery device posterior is provided with a PCO barrier edge distinct from the PCO barrier edge of the IOL. As shown in FIG. 7, the IOL system 11 includes the IOL 12 with haptics 28 extending from the lens 24. The drug delivery device 30 is disposed on the haptic, and, in this configuration, includes a posterior panel 33 with a posterior surface 33P which may or may not extend posteriorly beyond the plane (P) of the PCO barrier edge (shown in FIGS. 5 and 6), and an oblong aperture 34 which accommodates a portion of the haptic nearest the rim of the IOL lens which is oblong and mated to the oblong aperture. Two posts 35 extend anteriorly from the posterior panel 33 to join with an anterior panel 36 which is disposed on the anterior side of the haptic 28, forming the aperture 34 which is bounded by the posterior panel 33, anterior panel 36 and posts 35. As appears from FIG. 8, the posterior surface 33P of posterior panel 33 of the drug delivery device is joined to the side wall 33C of the posterior panel with a sharply angular edge 33E. This sharply angular edge may be similar to that of the sharply angular edge of the IOL, formed at the junction of the posterior surface 33P and the circumferential side wall 33C of the posterior side wall. The sharply angular edge 33E of the posterior panel may define a plane (D) which may be posterior to, or anterior to, or co-planar with, the plane (P) defined by the PCO barrier edge 24E of the IOL. Thus, the drug delivery device 30 is configured and disposed on the haptic 28 such that the sharply angular edge 33E of the drug delivery device 30 is anteriorly displaced from the plane (P), posteriorly displaced from the plane (P), or co-planar with the plane (P). FIG. 10 illustrates a configuration in which the plane (D) is posteriorly displaced from the plane (P) defined by the PCO barrier edge 24E of the IOL.

The sharply angular edge 33E of the posterior panel 33 preferably extends entirely around the posterior panel and side wall of the posterior panel. The sharply angular edge 33E of the posterior panel 33, and the circumferential side wall 33C may immediately abut the circumferential side wall 24C of the IOL, or the sharply angular edge 33E of the posterior panel 33, and the circumferential side wall 33C may be spaced from the circumferential side wall 24C, leaving a small radial gap between the PCO barrier edge of the IOL and the PCO barrier edge of the posterior panel 33, such that the circumferential side wall 33C of the posterior panel 33 is radially, outwardly displaced from the side wall 24C of the IOL 24.

If the plane (D) is coplanar with the plane (P), and the posterior panel directly abuts the IOL side wall, the area of the posterior panel directly abutting the IOL side wall may be provided with an edge that is not sharply angular, and the PCO barrier edge and remaining edge of the posterior panel will provide a sharply angular edge around entire periphery of the combined IOL and drug delivery device.

Figure 9:
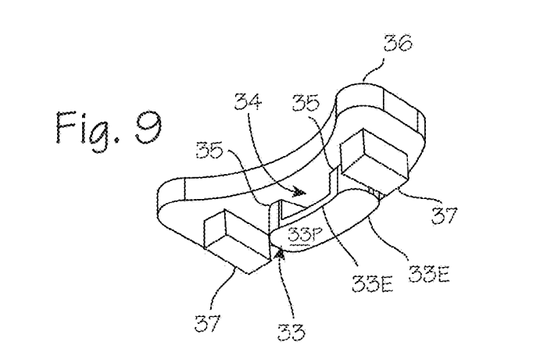
FIG. 9 shows the drug delivery device similar to that of FIG. 8 with the addition of additional panels or blocks depending from an anterior panel of the drug delivery device.

FIG. 8 shows the drug delivery device 30 of FIG. 7 in isolation, showing the aperture 34, posts 35 and posterior panel 33 and the anterior panel 36. FIG. 9 shows the drug delivery device 30 similar to that of FIG. 8 showing the apertures 34, posts 35 and posterior panel 33 and the anterior panel 36, with the addition of additional side panels or blocks 37. The side panels may extend posteriorly from the anterior panel, or they may be fixed to the posts. The portion of this drug delivery device which comprises a matrix material loaded with therapeutic agent, or an erodible therapeutic agent may include one or more, or all, of the anterior panel, posts, posterior panel or side panel(s).

In use, the IOL assembly and drug delivery device configurations of FIGS. 7, 8 and 9 may be implanted within the capsular bag of an eye of the patient, and the capsular bag may then approximate the IOL, and form a PCO barrier between the posterior portion of the capsular bag and the sharply angular edge of the IOL and form a PCO barrier between the capsular bag and the sharply angular edge of the posterior panel. The drug delivery device 30 will be secured on the haptic 28 such that a portion of the circumferential side wall 33C of the posterior panel 33 immediately abuts a portion of the side wall 24C of the IOL 24, or such that the circumferential side wall 33C of the posterior panel 33 is radially, outwardly displaced from the side wall 24C of the IOL 24, leaving a radial gap between the PCO barrier edge of the IOL and the PCO barrier edge of the posterior panel 33.

This may be accomplished by securing the drug delivery device 30 on the haptic 28 such that the sharply angular edge 33E of the drug delivery device 30 is anteriorly displaced from the plane (P), such that the sharply angular edge 33E of the drug delivery device 30 is posteriorly displaced from the plane (P), or such that the sharply angular edge 33E of the drug delivery device 30 is co-planar with the plane (P).

Figure 11:
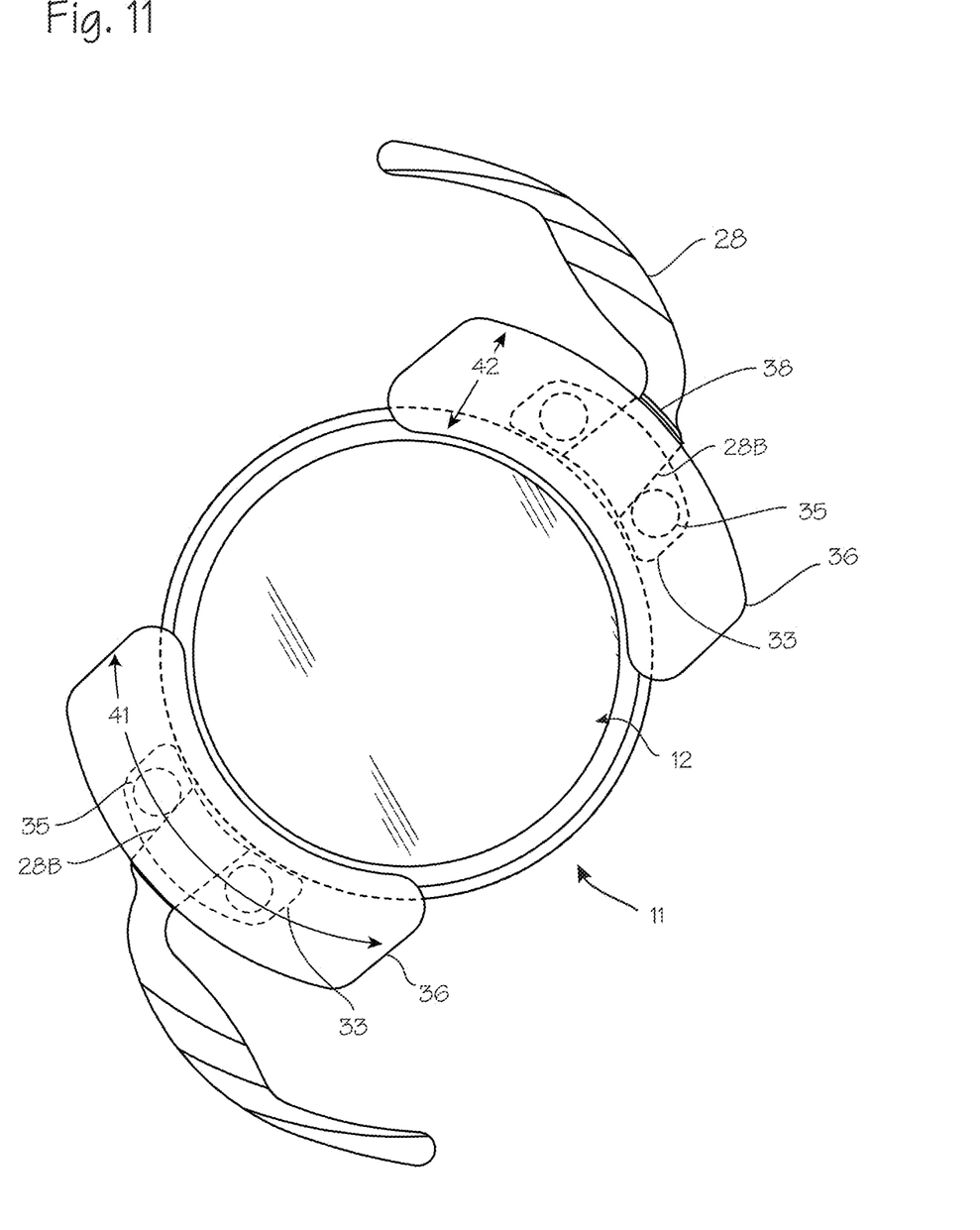
FIG. 11 illustrates a configuration of the drug delivery device and the haptic configured to avoid twisting of the drug delivery device about the haptic.

Various configurations of the drug delivery device may be employed to ensure that the IOL assembly 11, once implanted, remains in the preferred anterior/posterior position within the capsular bag, and remains in the desired orientation with the plane of the lens 24 perpendicular to the optical axis 10 of the eye, and, correspondingly, coplanar with the equatorial plane of the capsular bag, or in a plane parallel to the equatorial plane of the capsular bag. FIG. 11 illustrates a configuration of the drug delivery device 30 and the haptic 28. To avoid twisting of the drug delivery device about the haptic, the aperture through the drug delivery device (between the posterior panel and the anterior panel and connecting posts) is keyed to the shape of the base of the haptic, in any suitable manner and any suitable means, to inhibit or prevent rotation of the drug delivery device about the base of the haptic. In FIG. 11, this is accomplished with a haptic base 28B having a square or rectangular cross section, and a drug delivery device having a matching square or rectangular aperture sized to accommodate the haptic base. Thus, the drug delivery device is configured for disposition on the haptic, and the aperture is configured to accept the haptic base, and the aperture is correspondingly keyed to the shape and size of the haptic base in a configuration which inhibits rotation of the drug delivery device about the haptic base. In the assembled configuration, the drug delivery device is disposed on the haptic base, with the haptic base occupying the aperture. Any other configuration, in which the aperture is keyed to the haptic base, may be employed, such as an elliptical haptic base paired with an elliptical aperture, or a hexagonal haptic base paired with a hexagonal aperture in the drug delivery device. Thus, various means for preventing twisting of the drug delivery device about the haptic or haptic base may be employed.

Figure 12:
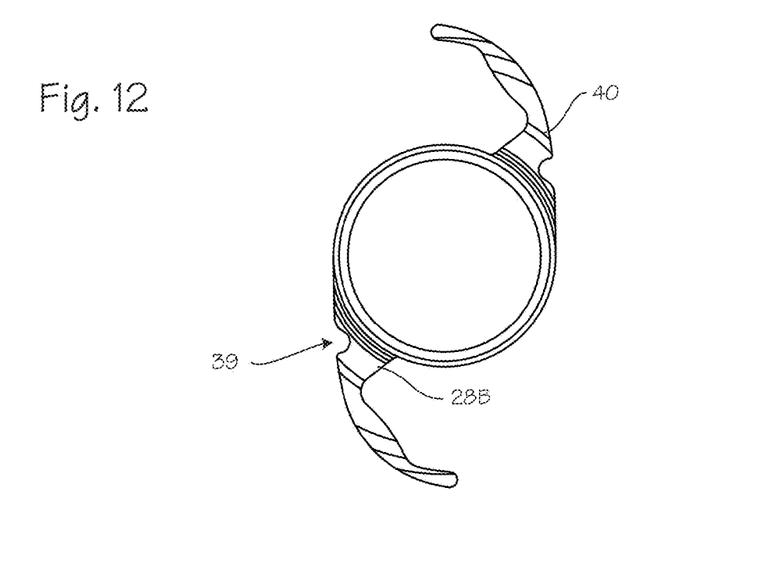
FIGS. 12 and 13 illustrate a means of preventing outward movement of the drug delivery device on the haptic, and features of the drug delivery device which prevent or limit twisting of the drug delivery device within the capsular bag.
Figure 13:
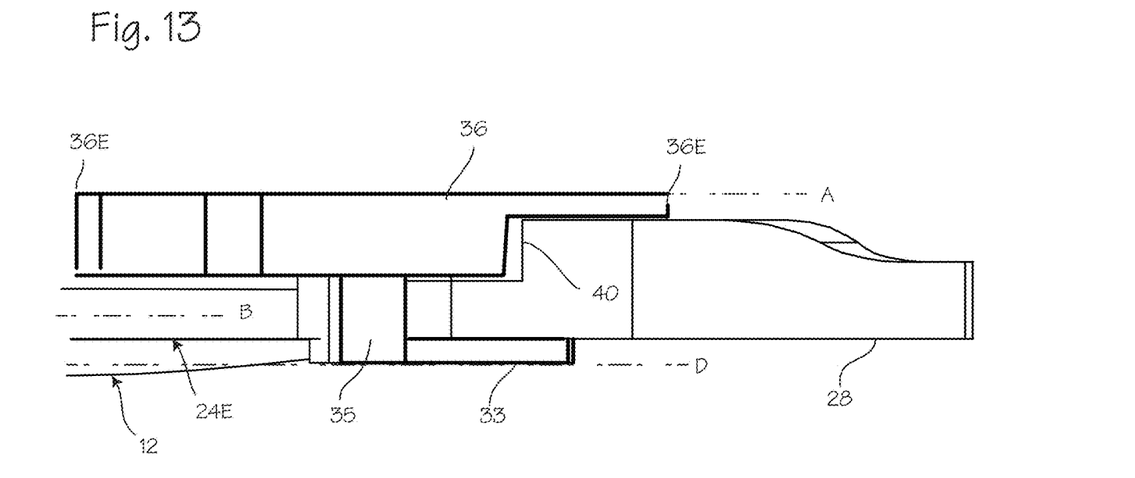

Means for preventing radially outward movement of the drug delivery device on the haptic may also be employed. As shown in FIG. 11 for example, the haptic may include a detent ridge 38 protruding from the haptic, with an optional corresponding detent accepting groove on the interior of the drug delivery device aperture. The drug delivery device may, once in place over the haptic base, impinge or abut the detent, thus preventing movement of the drug delivery device over the haptic. FIGS. 12 and 13 illustrate an embodiment of the haptic and drug delivery device, in which the haptic has a notch 39 disposed on the side of the haptic base 28B. The notch combined with a configuration of the post of the drug delivery device which fits within the notch provides an interference fit between the drug delivery device and the haptic. Once the drug delivery device is stretched over the haptic base, a post of the drug delivery device will fit within the notch, and the interference fit between the notch and the post will prevent outward migration of the drug delivery device.

FIGS. 12 and 13 illustrate another means of preventing outward movement, which includes a shoulder rising anteriorly from the haptic, combined with a shoulder on the anterior panel or plate of the drug delivery device. Once the drug delivery device is stretched over the haptic base, the drug delivery device will impinge on the shoulder and interfere with the shoulder and will prevent outward migration of the drug delivery device.

FIG. 13 also illustrates features of the drug delivery device which prevent or limit twisting of the drug delivery device with the capsular bag. The anterior panels are configured to limit the potential for twisting of the IOL relative the equator, or the plane established by the equator, of the capsular bag. Referring to FIG. 13, the anterior panel 36 has planar anterior surface 36A in which the entire edge 36E lies in a plane A, or a curved anterior surface in which the entire edge 36E lies in a plane A, and this planar surface or edge plane is disposed in a plane A which is parallel to the major plane of the IOL lens B, and, when properly implanted, the equatorial plane of the capsular bag (item 13 in FIG. 1). The anterior panel may have a large lateral or circumferential dimension compared to the radial dimension (FIG. 11) and the anterior surface of the anterior panel is preferably flat, and aligned in a plane parallel to the plane of the IOL. With this configuration, collapse of the capsular bag upon the IOL and the drug delivery device will be unlikely to exert forces on the IOL and drug delivery device which may twist or tilt the IOL within the capsular bag.

The IOL may be implanted by folding or rolling it into a small diameter configuration in an injector, inserting the injector through a small slit between the cornea and sclera, and pushing the IOL from the injector. Upon ejection from the injector, the IOL unfurls within the capsular bag and the haptics open and expand to the extent permitted by the confines of the capsular bag. The capsular bag will eventually collapse upon the IOL, and the posterior portion of the capsule will approximate the surfaces of the IOL, and in particular the sharp edge 24E. The tight join between the capsule and the sharp edge inhibits migration of lens epithelial cells to the region between the posterior portion of the capsule and the posterior surface of the IOL. The drug delivery device may be secured to the haptic upon manufacture, or it may be secured by the surgeon immediately before implantation, immediately after implantation, or long after implantation (for example as a replacement for an original drug delivery device which has been depleted).

In each embodiment described, the drug delivery device can be configured to deliver various therapeutic agents to treat various conditions. Brimonidine, latanoprost, timolol, pilocarpine, brinzolamide and other drugs in the general categories of beta blockers, alpha agonists, ROCK Inhibitors, adenosine receptor agonists, carbonic anhydrase inhibitors, adrenergic and cholinergic receptor activating agents, and prostaglandin analogues may be incorporated into the drug delivery devices to treat glaucoma. Aflibercept, bevacizumab, pegaptanib, ranibizumab, steroids, and aptamers may be incorporated into the drug delivery devices to treat wet macular degeneration. Complement factors, anti-oxidants and anti-inflammatory agents may be incorporated into the drug delivery devices to treat dry macular degeneration. Methotrexate, antibodies, dexamethasone, triamcinolone, and other steroid agents may be incorporated into the drug delivery devices to treat uveitis. Anti-proliferative agents, anti-mitotic agents, anti-inflammatory agents, and other medications that would inhibit the spread of lens epithelial cells may be incorporated into the drug delivery devices to treat posterior capsular opacification. Antibiotics such as fluoroquinolones, non-steroidal agents such as ketorolacs, and steroids such as prednisolones may be incorporated into the drug delivery devices for post-op management after cataract surgery to treat infection and inflammation.

While the configurations described above are described in the context of intraocular lens, each configuration may be employed with various other forms of ocular implants intended for implantation in the capsular bag, including capsular tension rings and capsular scaffolds.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. An ophthalmic implant comprising:
an IOL comprising a lens, and a haptic integrally formed with the lens and extending outwards therefrom, the IOL including an anterior surface, a posterior surface, and a circumferential side wall, wherein the posterior surface joins the circumferential side wall in a sharply angular edge, the sharply angular edge defining a plane of the sharply angular edge; and
a drug delivery device comprising an anterior panel and an aperture configured to receive a portion of the haptic therein, the drug delivery device configured and disposed on the haptic such that a posterior-most surface of the drug delivery device is anteriorly displaced from the plane.

2. The ophthalmic implant of claim 1, wherein:
the aperture is configured to accept a base portion of the haptic.

3. The ophthalmic implant of claim 2, wherein:
the aperture is keyed to a shape and size of the base portion of the haptic in a configuration which inhibits rotation of the drug delivery device about the base portion of the haptic.

4. The ophthalmic implant of claim 1, wherein:
the drug delivery device further comprises a posterior panel including the posterior-most surface, the aperture received over the haptic, the haptic being displaced anteriorly from the plane.

5. The ophthalmic implant of claim 4, wherein:
the posterior panel and the anterior panel of the drug delivery device are joined by a pair of posts, with the aperture bounded by the posterior panel, the anterior panel and the pair of posts.

6. The ophthalmic implant of claim 5, wherein:
the aperture is keyed to a shape and size of a base portion of the haptic in a configuration which inhibits rotation of the drug delivery device about the base portion of the haptic.

7. The ophthalmic implant of claim 1 wherein:
the posterior-most surface of the drug delivery device is anteriorly displaced from the plane by 0.1 to 1 millimeters.

8. The ophthalmic implant of claim 1 wherein:
the haptic is joined to the lens at a joint, and a posterior-most extent of the joint between the haptic and the lens is displaced anteriorly from the sharply angular edge.

9. The ophthalmic implant of claim 1 wherein:
the haptic is joined to the lens at a joint, and a posterior-most extent of the joint is displaced anteriorly from the sharply angular edge, wherein the presence of the haptic does not disrupt formation of a PCO barrier between the sharply angular edge and a posterior portion of a capsule.

10. The ophthalmic implant of claim 1, wherein:
the sharply angular edge is characterized by an inside angle and a corner radius between a posterior panel surface and the circumferential side wall of a posterior panel, the inside angle of the sharply angular edge is in a range of 80° to 100°, and the corner radius of the sharply angular edge is less than 500 μm.

11. The ophthalmic implant of claim 1, wherein:
the drug delivery device comprises one or more therapeutic agents.

12. The ophthalmic implant of claim 11, wherein:
the one or more therapeutic agents comprise a beta blocker, an alpha agonist, a ROCK inhibitor, an adenosine receptor agonist, a carbonic anhydrase inhibitor, an adrenergic or cholinergic receptor activating agent, a prostaglandin analogue, a steroid, an aptamer, an antibody, a complement factor, an anti-oxidant, an anti-inflammatory agent, an anti-proliferative agent, an anti-mitotic agent, an antibiotic, or any combination thereof.

13. The ophthalmic implant of claim 11,
wherein the one or more therapeutic agents comprise a prostaglandin analogue.

14. The ophthalmic implant of claim 1, wherein the presence of the drug delivery device on the haptic does not disrupt formation of a PCO barrier.

15. The ophthalmic implant of claim 1, wherein the anterior panel includes a planar anterior surface.

16. An ophthalmic implant comprising:
an IOL comprising a lens, a first haptic extending outwards from the lens, a second haptic extending outwards from the lens, an anterior surface, a posterior surface, and a circumferential side wall, wherein the posterior surface joins the circumferential side wall in a sharply angular edge, the sharply angular edge defining a plane of the sharply angular edge; and
first and second drug delivery devices, the first drug delivery device disposed on the first haptic and including a first anterior panel, the second drug delivery device disposed on the second haptic and including a second anterior panel, wherein a posterior-most surface of the first and the second drug delivery devices is anteriorly displaced from the plane.

17. The ophthalmic implant of claim 16, wherein the first drug delivery device includes a first aperture, and the second drug delivery device includes a second aperture, the first haptic received through the first aperture, the second haptic received through the second aperture.

18. The ophthalmic implant of claim 17, wherein the first and the second apertures are keyed to a shape and size of the first and the second haptics, respectively, such that rotation of the first haptic relative to the first aperture and the second haptic relative to the second aperture are inhibited.

19. The ophthalmic implant of claim 18, wherein:
the first drug delivery device comprises a first posterior panel operably coupled to the first anterior panel, the second drug delivery device comprises a second posterior panel operably coupled to the second anterior panel.

20. The ophthalmic implant of claim 19, wherein:
the first posterior panel and the first anterior panel are joined by a first pair of posts, with the first aperture bounded by the first posterior panel, the first anterior panel and the first pair of posts, and
the second posterior panel and the second anterior panel are joined by a second pair of posts, with the second aperture bounded by the second posterior panel, the second anterior panel and the second pair of posts.

21. The ophthalmic implant of claim 16, whereby the presence of the first and the second drug delivery devices on the first and the second haptics, respectively, do not disrupt formation of a PCO barrier.

22. The ophthalmic implant of claim 16, wherein:
the first haptic is joined to the lens at a first joint having a first posterior-most extent, the second haptic is joined to the lens at a second joint having a second posterior-most extent, the first posterior-most extent and the second posterior-most extent are displaced anteriorly from the sharply angular edge.

23. The ophthalmic implant of claim 16, wherein:
the first and the second drug delivery devices comprise one or more therapeutic agents.

24. The ophthalmic implant of claim 23, wherein:
the one or more therapeutic agents comprise a beta blocker, an alpha agonist, a ROCK inhibitor, an adenosine receptor agonist, a carbonic anhydrase inhibitor, an adrenergic or cholinergic receptor activating agent, a prostaglandin analogue, a steroid, an aptamer, an antibody, a complement factor, an anti-oxidant, an anti-inflammatory agent, an anti-proliferative agent, an anti-mitotic agent, an antibiotic, or any combination thereof.

25. The ophthalmic implant of claim 23, wherein the one or more therapeutic agents comprise a prostaglandin analogue.

26. The ophthalmic implant of claim 16, wherein the first anterior panel includes a first planar anterior surface, and the second anterior panel includes a second planar anterior surface.

* * * * *